United States Patent [19]
Gugger et al.

[11] Patent No.: US 6,171,638 B1
[45] Date of Patent: *Jan. 9, 2001

[54] PRODUCTION OF ISOFLAVONE ENRICHED FRACTIONS FROM SOY PROTEIN EXTRACTS

[75] Inventors: Eric Gugger; Richard Grabiel, both of Decatur, IL (US)

[73] Assignee: Archer Daniels Midland Company, Decataur, IL (US)

[*] Notice: Under 35 U.S.C. 154(b), the term of this patent shall be extended for 0 days.

This patent is subject to a terminal disclaimer.

[21] Appl. No.: 09/478,751

[22] Filed: Jan. 6, 2000

Related U.S. Application Data

[63] Continuation-in-part of application No. 09/035,588, filed on Mar. 5, 1998, now Pat. No. 6,033,714, which is a continuation-in-part of application No. 08/868,629, filed on Jun. 4, 1997, now Pat. No. 5,792,503, which is a division of application No. 08/614,545, filed on Mar. 13, 1996, now Pat. No. 5,702,752.

[51] Int. Cl.[7] .................................................. A23L 1/20
[52] U.S. Cl. ........................ 426/634; 426/429; 426/431; 426/490; 426/520; 549/403
[58] Field of Search ................... 426/429, 431, 426/443, 478, 490, 492, 520, 634, 648, 425; 549/403

[56] References Cited

U.S. PATENT DOCUMENTS 5,702,752 * 12/1997 Gugger et al. ...................... 426/634
5,792,503 *  8/1998 Gugger et al. ...................... 426/634
6,033,714 *  3/2000 Gugger et al. ...................... 426/634

* cited by examiner

Primary Examiner—Milton Cano
(74) Attorney, Agent, or Firm—Laff, Whitsel & Saret, Ltd.; J. Warren Whitesel

[57] ABSTRACT

The temperature sensitive differential of the solubilities of various isoflavone fractions is used to initially separate the fractions by heating an aqueous soy molasses or soy whey feed stream. The temperature of the feed stream is selected according to the temperature at which a desired isoflavone fraction or fractions become soluble. Then, the heated feed stream is passed through an ultrafiltration membrane or reverse osmosis in order to concentrate the solids. The resulting permeate is put through a resin adsorption process carried out in at least one liquid chromatography column to further separate the desired isoflavone fractions. Various processes are described for drying and crystallizing the isoflavone fractions to a powder. A solvent is then added to the isoflavone fraction to dissolve impurities and rehydrate the dry powder. Usually, the rehydrated isoflavone is used as an ingredient in a food ingredient or food product. At various points in the process a selected amount of isoflavones may or may not be blended with the powder in order to bring the isoflavone to a desired characteristic specification or to produce a food ingredient or food product.

62 Claims, 4 Drawing Sheets

PRODUCTION OF ISOFLAVONE ENRICHED FRACTIONS FROM SOY PROTEIN EXTRACTS

This is a continuation-in-part of Ser. No. 09/035,588, filed Mar. 5, 1998, now U.S. Pat. No. 6,033,714, which in turn is a continuation-in-part of Ser. No. 08/868,629, filed Jun. 4, 1997, now U.S. Pat. No. 5,792,503, which in turn is a division of Ser. No. 08/614,545, filed Mar. 13, 1996, now U.S. Pat. No. 5,702,752.

The invention relates to processes for producing isoflavone fractions by a treatment of an aqueous alcohol extract of defatted soybean flakes.

BACKGROUND OF THE INVENTION

As used herein, the term "isoflavone forms" includes malonyl, acetyl, glucoside, and aglycone forms of the isoflavones.

This invention will find use when processing any one of a number of plants or plant material, the preferred one of which is the soybean.

Those who are skilled in the art will readily perceive a variety of other plants or plant material which may be used, for example, kudzu and subterranean clover are also expected to work in this invention. Accordingly, the terms plant, plant material, and vegetable are to be construed herein as including these and other suitable materials.

For some background information on processing soy, reference may be made to the following articles: "*Isolated Soy Protein*" by C. W. Kolar, S. H. Richert, C. D. Decker, F. H. Steinke, and R. J. VanderZanden, found as chapter VIII of *New Protein Foods*, Vo. 5, eds. Aaron M. Altschul and Harold L. Wilcke, Academic Press, Inc. 1985; "*Traditional Soyfoods: Processing and Production*" by Peter Goldbitz; and "*Soy Protein Products; Processing and Use*" by Edmund W. Lucas and Mian N. Raz, both (0022-3166/95) published 1995 by the American Institute of Nutrition. A process for producing soy whey is disclosed on pages 386, 387 of "*Soybeans Chemistry, Technology, and Utilization*" by KeShun Liu, published by Chapman & Hall, 115 Fifth Avenue, New York, N.Y. 10003.

Isoflavones are a unique class of plant flavonoids that have a limited distribution in the plant kingdom and may be physically described as colorless, crystalline ketones. The most common and important dietary source of these isoflavones are soybeans which contain the following twelve isoflavone isomers: genistein, genistin, 6"-0-malonylgenistin, 6"-0-acetylgenistin, daidzein, daidzein, 6"-0-malonyldaidzein, 6"-0-acetylgenistin; glycitein, glycitin, 6"-0-malonylglycitin, 6"-0-acetylglycitin (Kudou, Agric. Biol. Chem. 1991, 55, 2227–2233). Ninety-seven to ninety-eight percent of the soybean isoflavones are in the glycosylated form.

Traditionally, individuals have been limited in their use of soy foods to increase their levels of dietary isoflavones because the number and variety of soy foods available in the U.S. marketplace is limited. Also, natural flavors and color of some soy products have been described as bitter and unappetizing.

The isoflavone, genistin, was first isolated from soybean meal in 1931 by Walz (Justus Liebigs Ann. Chem 489, 118) and later confirmed in 1941 by Walter (J. Amer. Chem. Soc. 63, 3273). Patents have described the production of isoflavone enriched soy-protein products (WO 95/10512, WO 95/10529; WO 95/10530), genistin malonate and daidzen malonate (U.S. Pat. No. 5,141,746), pharmaceutical-type compositions containing isoflavones (U.S. Pat. Nos. 5,424,331; 4,883,788), and isolation and modification of isoflavones from tempeh (U.S. Pat. Nos. 4,390,559; 4,366,248; 4,366,082; 4,264,509; 4,232,122; 4,157,984). The present patent relates to the manufacture of highly enriched isoflavone products containing either a wide-range of soy isoflavones or highly-purified genistin gained from an ethanol extract of defatted soybean flakes.

Coronary heart disease (CHD) is a leading cause of death, especially in the United States and other industrialized nations. Elevated total and low density lipoprotein (LDL) cholesterol levels are important risk factors for CHD. In humans, soy protein products appear to lower serum total cholesterol levels by an average of about 9.3% and to lower low-density lipoprotein (LDL) cholesterol by an average of about 12.9% when consumed at an average intake level of 47 g soy protein per day (Anderson et al., *NEJM*, 333: 276–282, 1995).

Isoflavones (Phytoestrogens) are implicated as a class of compounds in soy protein products which is at least partly responsible for this cholesterol-lowering effect in animals (Setchell, in McLachlan JA, ed. Estrogens in the Environment II: 69–85, 1985). In addition, studies with primates suggest that soy isoflavones may account for up to about 60–70% of the hypochoesterolemic properties of soy protein (Anthony et al., Circulation, 90: Suppl: I-235 (abstract), 1994; Anthony et al., J. Nutr., 125: Suppl 3S: 803S–804S (abstract), 1995; Anthony et al., Circulation, 91: 925 (abstract), 1995).

It has also been suggested that isoflavones have an ability to play a role in the prevention of certain cancers. Japanese women who have consumed diets rich in isoflavones appear to have a very low incidence of breast cancer (Adlercreutz et al., J. Nutr. 125: 757S–770S, 1995). Soy products have also been shown to decrease mammary tumor formation or to inhibit mammary tumor progression in rat breast cancer models (Barnes et al., Clin. Biol. Res. 347: 239–253; Hawrylewicz et al., J. Nutr. 121: 1693–1698, 1991). Genistein has been shown to inhibit protein tyrosine kinase (Akiyama et al., J. Biol. Chem. 262: 5592–5595, 1987), to inhibit angiogenesis (Fotsis et al., Proc. Natl. Acad. Sci. USA 90: 2690–2694, 1993), and to induce differentiation in several malignant cell lines (Peterson, J. Nutr. 125: 784S–789S, 1995), all of which may be important risk factors in cancer development. Genistein and Biochanin A also appear to inhibit the growth of androgen-dependent and independent prostatic cancer cells in vitro (Peterson and Barnes, Prostate 22: 335–345, 1993). Genistein may act as an antioxidant (Wei et al., Nutr. Cancer 20: 1–12, 1993).

Beyond cancer, it is thought that at least some of the soy isoflavone fractions were especially beneficial for women in general since it is a source of plant estrogen. It is thought that plant estrogen provides many of the advantages and avoids some of the alleged disadvantages of animal estrogen. Hence, it is especially desirable to enable the isoflavone fractions to be used in a wide variety of ways, such as in beverages and foods. This means that the isoflavone fractions should not introduce unacceptable tastes or unappetizing colors.

The process described in the above-cited U.S. Pat. No. 5,702,752 produces an excellent concentration of isoflavones. However, the end product could be improved because it had a color and flavor which sometimes tended to limit its desirability. For example, there has been a tendency to think that soy isoflavone fractions should be limited to uses where the consumer does not either taste or really see it, as when the isoflavones are formed into tablets, pills, or capsules.

There are other uses for isoflavones which are desired. For example, there are times when it is desirable to use the isoflavones in foods, beverages, medical foods, and certain dietary supplement products.

SUMMARY OF THE INVENTION

Accordingly, an object of this invention is to provide isoflavone fractions which have a neutral color and a blank flavor. These fractions may consist of one or more compound types of isoflavones as well as one or more derivatives of these forms. In particular, an object is to provide an ingredient which may be included in a great variety of foods and beverages. More particularly, an object is to provide materials where smaller quantities of an ingredient deliver the same amount or more of the desired isoflavones.

Another object is to provide a process that uses soy whey, which has sometimes been an unacceptable starting material for use in more important and valuable products; therefore, it is often generated as a by-product of soy processing.

A still further object of the invention is to provide a process that results in an intermediate product that can be conveniently stored for later processing into a pure form when required. Another object is to provide a process that requires less equipment and less time to produce a more consistently pure product.

In keeping with an aspect of the invention, these and other objects are accomplished by starting preferably with soy molasses, or alternatively with soy whey, which is subjected to ultra-filtration in order to produce a permeate which then passes through a column containing an adsorbing resin. The resin is then washed with water and eluted with aqueous alcohol, preferably ethanol. Next the alcohol is evaporated until the solids are in the range of approximately 1–20% of the remaining liquid. The resulting product is dried, preferably by spray drying or by another appropriate means. The dried product may then optionally be stored, or may be immediately further processed by adding a solvent, preferably water, to dissolve the soluble fraction of the dried product, which is enriched in the undesirable color and flavor fractions. The non-soluble fraction, which is enriched in isoflavones, can then be separated from the soluble fraction by any conventional means, and dried preferably by spray drying.

In keeping with a further aspect of the invention, and in order to fine tune the characteristics of the product, the product is dried to a powder. Then, a plurality of lots may be blended together to achieve a standard isoflavone level. When the product is ready for use as, for example, a food ingredient or the like, the blended product may be rehydrated. There are many advantages resulting from the process of drying, adding an ingredient, blending, and then rehydrating since it permits storage in a dry form, better blending, and closer control over the specifications of the final product. It is easier to control product specifications by a blending of optimally selected dry ingredients. Also, dry storage smoothes production and enables sudden large orders to be filled quickly. Thus, quality control is made easier.

In addition, there is less equipment usage since it is no longer necessary to have large batches of product sitting in expensive tanks over long periods of time (often as much as two days) during which crystals are separated from their mother liquid. Since the product may be held in storage in a dry form, there is a less likelihood that contamination might occur. There is a larger commercial market for dry powder then there is for a liquid product. The dry product better enables a final usage in many forms such as pill, liquids, ingredients for various foods, and the like.

BRIEF DESCRIPTION OF DRAWINGS

These and other objects of this invention will become more apparent from the following specification taken with the attached drawings, in which.

DETAILED DESCRIPTION OF THE INVENTION

This invention employs methods based on the differential solubilities of isoflavones in aqueous solutions. Genistin is the least water soluble of the isoflavone glycosides, is mostly insoluble in cold water, and is only slightly soluble in hot water (FIG. 1).

Figure 1:
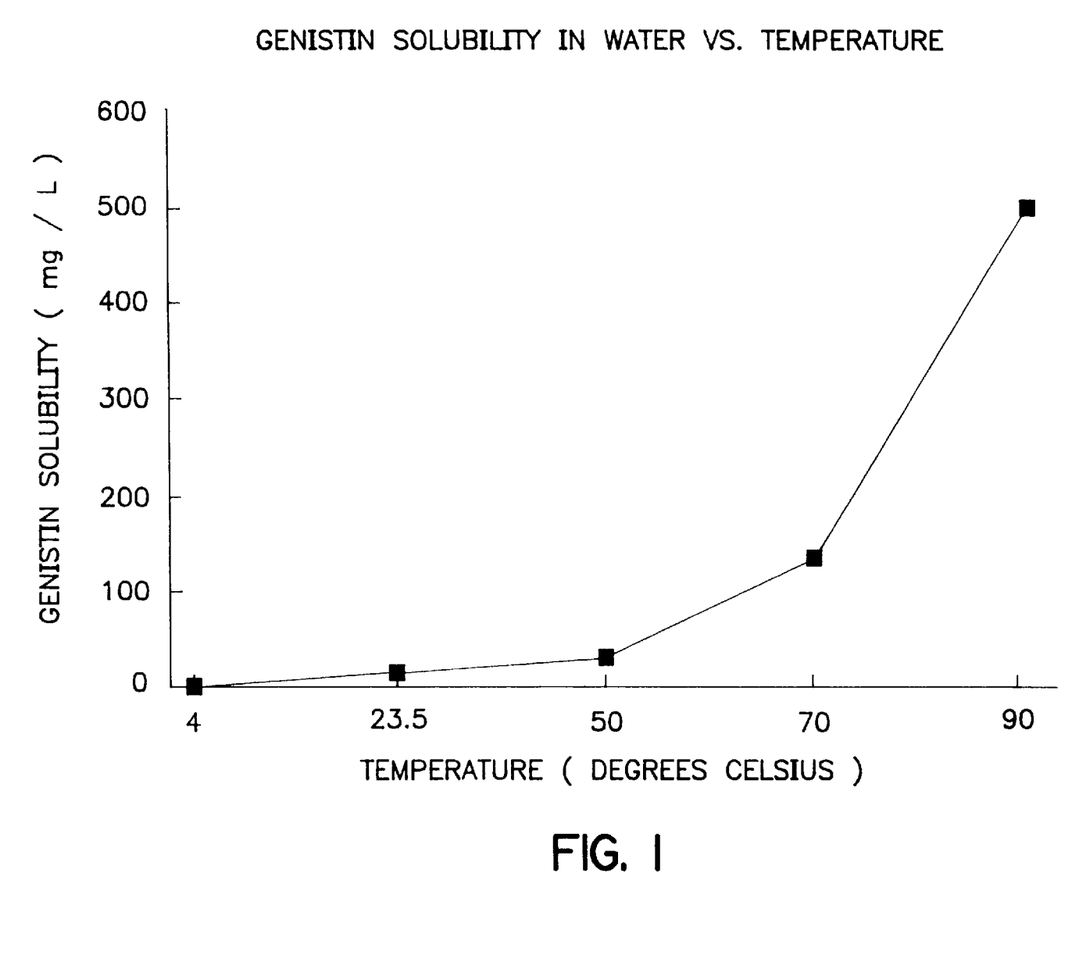
FIG. 1 is a graph showing the solubility of genistin in water vs. temperature.

In greater detail, FIG. 1 shows that the solubility of genistin is practically unchanged as the temperature increases from 4° C. to 50° C., but that the solubility increases rapidly as the temperature increases from 70° C. to 90° C. Therefore, if the manufacturing process is to recover genistin, the recovery step should be carried out at the high temperature end of the scale.

All isoflavone glycosides other than genistin have higher solubilities in water and readily pass through an ultrafiltration membrane, along with other water soluble components. By increasing the temperature of the aqueous solution prior to ultrafiltration, genistin and all other isoflavones can be separated from insoluble materials. The isoflavones in the ultrafiltration permeate can be recovered by treating the solution with resin, washing the resin with water to remove soluble sugars, and eluting the isoflavones with a mixture of ethanol and water, followed by drying.

The starting material for the inventive processes is derived from an aqueous ethanol extract of hexane-defatted soybean flakes. The defatted soybean flakes are extracted with aqueous ethanol (approximately 60–80% ethanon by volume) at temperatures in the range of about 44°–63° C. or 120°–150° F. This aqueous ethanol extract is then subjected to a vacuum distillation in order to remove ethanol. The alcohol-stripped extract is also known as "soy molasses" or "soy solubles." Soy molasses often is a by-product of processes which make soy protein concentrate.

An alternative starting material is soy whey. The whey may be made in any of many well-known ways, one of which is shown on page 387 of the above-cited book "Soybeans" by KeShun Liu. In general, this Liu process begins with defatted soy meal which is passed through an aqueous extraction of pH 9.0. Then, the aqueous material is centrifuged followed by an isoelectric precipitation at a pH 4.5. The resulting material is separated into curd and whey. The curd is further processed into soy protein isolate.

Then the extract (either molasses or whey) is adjusted within an appropriate temperature range (about 65–95° C.)

and subjected to ultrafiltration preferably by using a 100,000 molecular weight cut-off (MWCO) membrane. However, the process is not limited to this 100,000 cut-off membrane since any membrane or ceramic element which enables a filtration of the desired isoflavones may be used, such as a membrane in the range of 600–1,000,000 molecular weight cut-off. The smallest cut-off membrane suitable for the inventive procedures should pass a molecular weight of 532, which provides a sufficient retention of insoluble material and passage of isoflavones. Moreover, ultrafiltration may be performed on the basis of size, rather than molecular weight. Size, of course, often correlates roughly with molecular weight. An 0.1 micron membrane is another preferred membrane.

Figure 2:
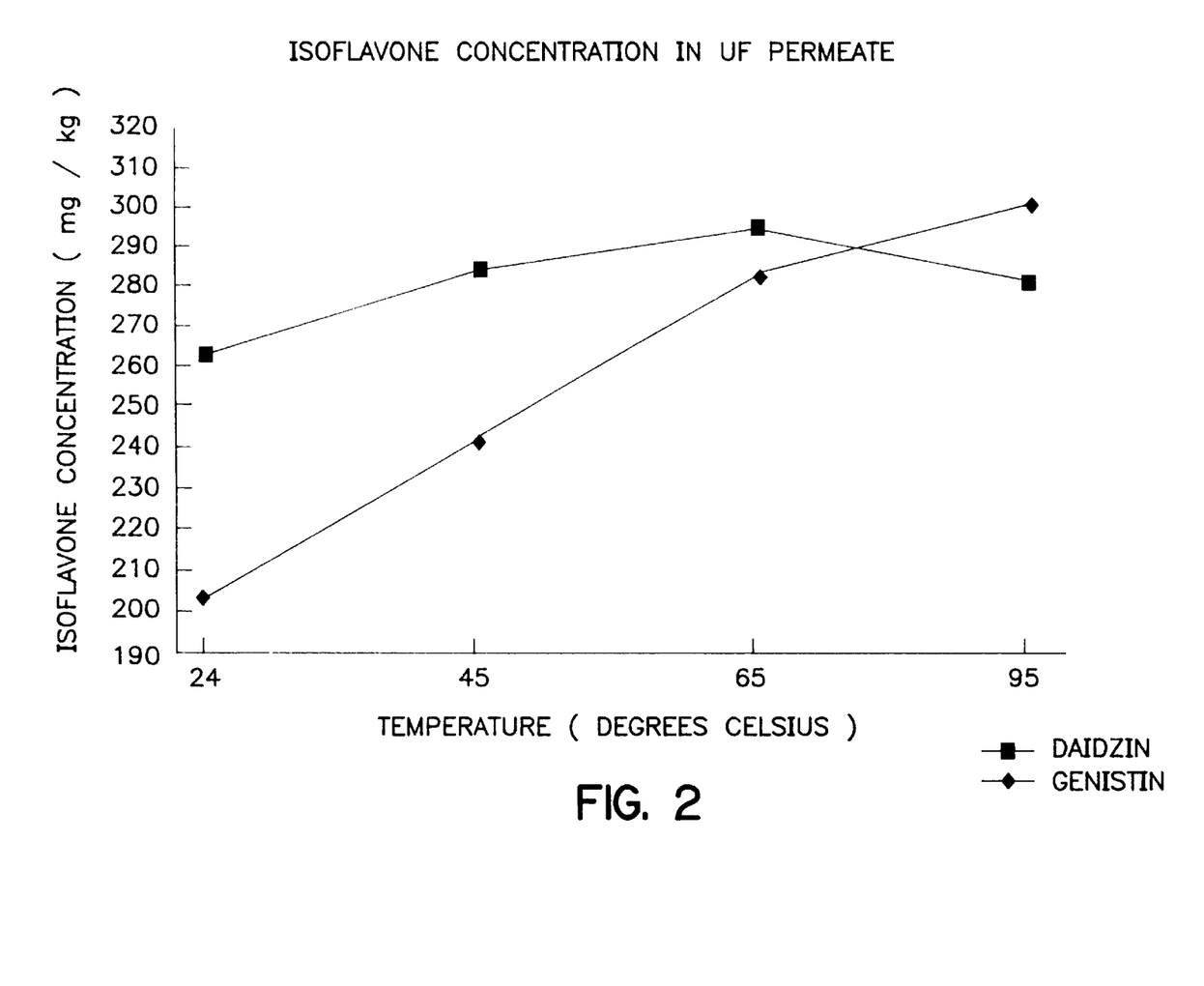
FIG. 2 is a graph showing the concentration of isoflavone in a UF permeate vs. temperature.

The effect of temperature on the concentration of two principal isoflavones, daidzein and genistin, in the UF permeate, is shown in FIG. 2. Cooler temperatures result in lower concentrations of genistin in the UF permeate. daidzein concentrations are much less affected by temperature. To achieve optimal concentrations of isoflavones in the UF permeate, ultrafiltration should be carried out at a temperature above 65° C.

For example, FIG. 2 shows the differential between the concentration of daidzein and genistin in an aqueous solution permeate subjected to ultrafiltration. Ultrafiltration at 24° C. produces a high concentration of daidzein and a low concentration of genistin. Therefore, if the manufacturing step is to recover daidzein and reject genistin, perhaps the recovery should be carried out at the relatively low temperature of 24° C., although the exact temperature may be selected on a basis of how much genistin can be located in the permeate. On the other hand, if the manufacturing process is designed to recover both daidzein and genistin, perhaps it would be better to operate at the crossover point of about 78° C. For genistin, recovery should be carried out at a higher temperature.

Figures 3, 4:
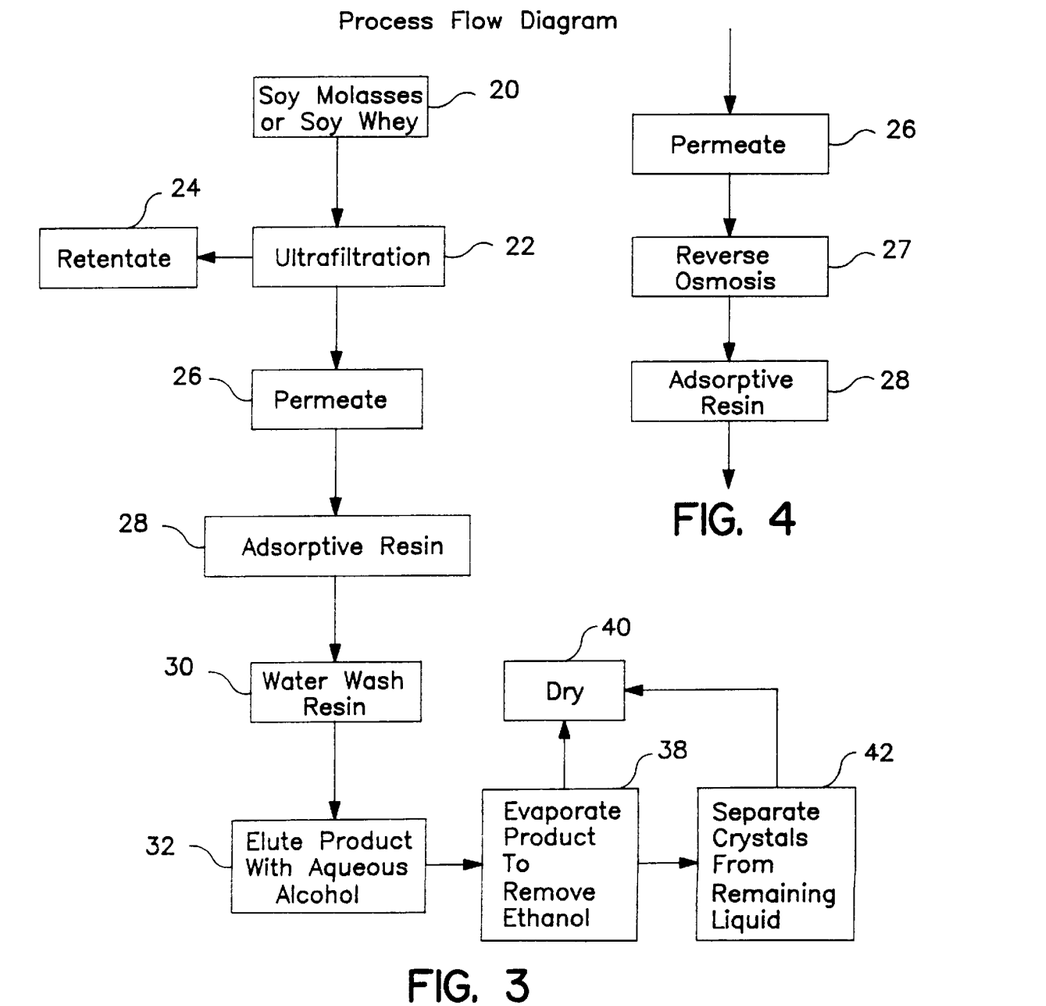
FIG. 3 is a process flow diagram showing the production of the inventive product.
FIG. 4 is a fragment of FIG. 3 including a reverse osmosis step.

A flow diagram representing one example of a manufacturing processes is shown in FIG. 3.

In greater detail, FIG. 3 shows at 20 that the preferred starting material is either soy molasses or soy whey which is subjected to ultrafiltration at 22. At 24, the retentate of the ultrafiltration is further processed, recycled, or otherwise used in another process.

If a batch type process is employed, the volume of the UF retentate fraction 24 is reduced during the ultrafiltration process by about one-third to two-thirds of the original alcohol-stripped extract volume, or stated otherwise is up to 12–15% solids. The UF retentate may be diafiltered with about one to three retentate volumes of water, which has been previously adjusted to be within a temperature range of about 65–95° C. in order to recover a greater percentage of isoflavones in the permeate. The retentate will then be used in some other process having no direct relationship with the process shown in FIG. 3.

With or without the diafiltered permeate, the ultrafiltration permeate at 26 contains a variety of isoflavones and is adjusted to an appropriate temperature (45–95° C.). Then, it is treated with an adsorptive resin at 28 in either a batch or, preferably, chromatography column type process. As shown in FIG. 4, in some examples, a reverse osmosis step 27 may be included between the permeate step 26 and the adsorptive step 28.

More preferably, a continuous process is designed to use a plurality of chromatography columns wherein one column is loading while another column is eluting with still other columns in various stages between loading and eluting. This way, there may be a continuously flowing stream of finished product. There are a number or resins which may be used in the chromatography column. The resin may be, but is not limited to, ethylvinylbenzene-divinyl-benzene, styrene-divinyl-benzene or polystyrene polymers or copolymers, and may be either ionic or non-ionic.

A particularly attractive resin for use in the inventive process is "Amberlite" XAD-4 polymeric adsorbent sold by the Rohm and Haas Company at the Independence Mall West, Philadelphia, Pa. 19105. The manufacturer describes this resin as a non-ionic polymeric adsorbent supplied as insoluble white, cross-linked polymer beads which derives its adsorptive properties from its macroreticular structure containing both a continuous polymer phase and a continuous pore phase. This structure gives this polymeric adsorbent excellent physical, chemical, and thermal stability. "Amberlite" XAD-4 polymeric adsorbent is further described as capable of being used through repeated cycles, in columns or batch modes, to adsorb hydrophobic molecules from polar solvents or volatile organic compounds from vapor streams. Its characteristic pore size distribution is said to make "Amberlite" XAD-4 polymeric adsorbent a choice for the adsorption of organic substances of relatively low molecular weight.

The physical properties of "Amberlite" XAD-4 are described by this manufacturer as follows:

| | |
|---|---|
| Matrix | Macroreticular cross-linked aromatic polymer |
| Appearance | White translucent beads |
| Particle Size | 0.3–1.2 mm (90% within) |
| True Wet Density | 1.02 g/ml |
| Surface Area | 800 m$^2$/g minimum |
| Porosity | 55% (vol/vol) minimum |
| Pore Size Range | 1–150A |

Following passage through the chromatography columns, the resin is washed with water at 30. Next, the isoflavones are eluted at 32 with an aqueous alcohol such as ethanol, methanol, or isopropanol (20–100% by volume, at 25–85° C.) as either a gradient or single percentage process. Here, 80% ethanol is preferred at a temperature of 40–70° C.

At 38, the resulting material is evaporated to provide a liquid having about 1–20% dry solid material in order to begin crystallization by removing the alcohol used in step 32. The evaporated product may then be further processed by spray drying at 40. The resulting dried material is approximately reddish-brown and approximately 20–60% by weight isoflavones on a solids basis. It is thought that the most usual range for such dried material produced from soy molasses is about 30–50% wt isoflavones and from soy whey is about 20–40% wt isoflavones which seems to depend on the isoflavone concentration in the starting material, feed loading, and other variables. Or, further processing may be carried out by adjusting the evaporated product to an appropriate temperature (4–45° C.) to promote crystallization of isoflavone fractions.

These crystals can then be separated by settling, decanting, centrifuging, or filtering crystals at 42, to produce the resulting product which is cream colored, bland tasting, and about 50–90% wt isoflavones upon drying. It is thought that decanting, centrifugal filtration or using Hydroclone® machinery available from Dorr-Oliver in Milford, Conn. will also work for such separation. When produced from soy molasses, the resulting crystalline product is most usually 70–90% wt isoflavones and when produced from soy whey, is most usually 50–80% wt isoflavones.

Figures 5, 6:
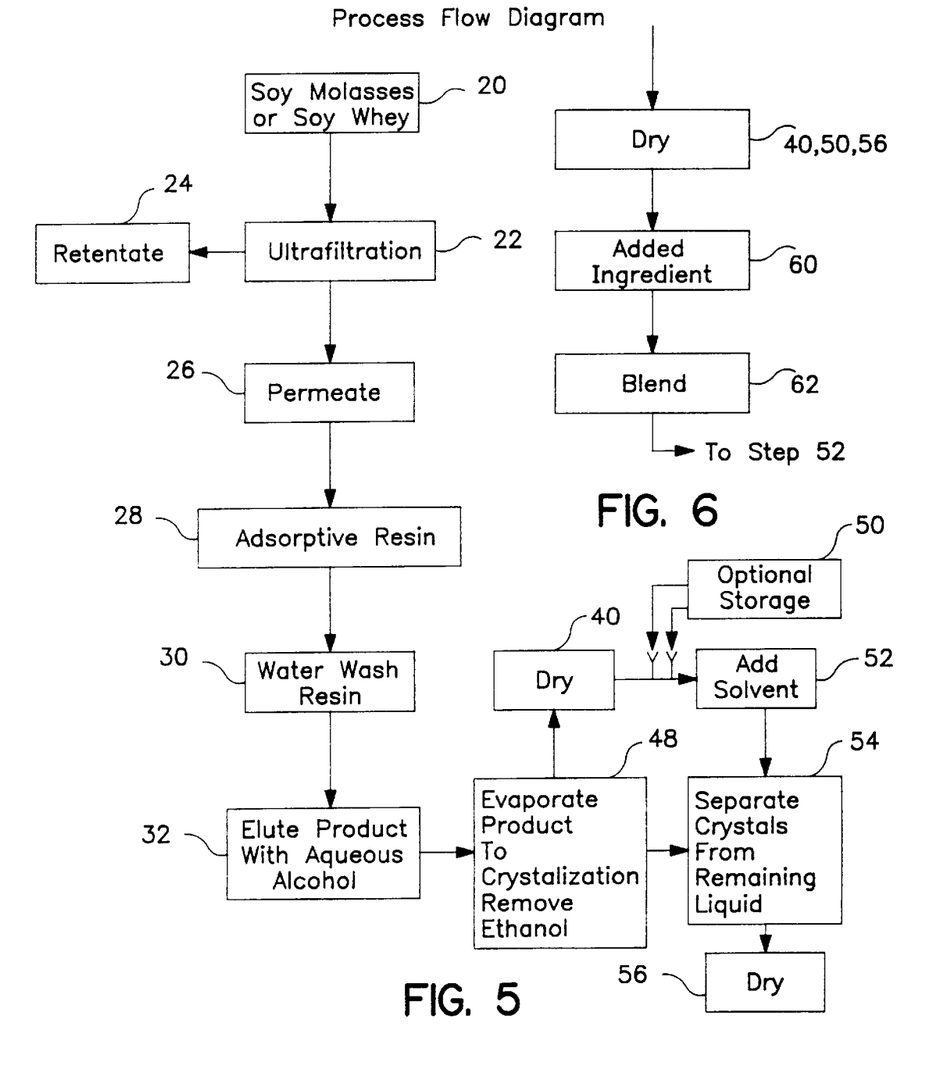
FIG. 5 is a process flow diagram showing a new method of production of the inventive product.
FIG. 6 is a fragment of FIG. 4 including a step of blending the inventive product with an added ingredient.

A flow diagram representing one example of a manufacturing process is shown in FIG. 5, where the product is dried for storage, blending, etc., and then rehydrated for its end use.

FIG. 5 shows a process which is the same as the process shown in FIG. 3, from step 20 through step 32. Therefore, these steps will not be explained again.

At step 48, the product stream is evaporated to remove ethanol and promote crystallization of the isoflavones. From step 48, the product stream is sent into any suitable dryer 40 (such as a spray dryer, for example) where the crystals are reduced to a dry powder. Depending upon the needs of any particular production run, the dry powder may be stored at 50.

When the time comes to further continue the process, the powders extracted from either the dryer 40 or the optional storage 50 are treated with a suitable solvent at 52. This solvent preferentially dissolves the colors and flavors, while the isoflavones remain preferentially undissolved, allowing for an relatively inexpensive further purification of the isoflavones. The solvent is preferably selected from the group of tap water, deionized water, distilled water, ethanol, isopropanol, methanol, and combinations of these solvents. In the preferred form, water is used. In the most preferred form, tap water is used. Step 52 works at a range of temperatures, from at least about 4° C. to at least about 95° C., and the preferred range is about 10–70° C., with the more preferred range being about 20–40° C. Step 52 also works at a range of pH, from at least about 2 pH to about 10 pH, with the preferred pH being about 6–8 pH.

Then at 54, the crystals are separated from the impurities and solvent and thereafter dried by any suitable dryer (such as a spray dryer) a second time at 56. The resulting dried material is very light tan, bland tasting, and approximately 60–90% isoflavones on a solids basis.

Also, at step 54, the undissolved isoflavones are separated from the solvent, removing much of the undesired colors and flavors. It is believed that, particularly when water is used as the solvent, the separated solvent may be enriched in saponins or forms of daidzein. Thus, the separated non-solids may be of utility in processes calling for saponins or forms of daidzein.

In order to fine tune the characteristics of the product, the dry powder resulting from step 40, 50, or 56 (FIG. 6) may be blended with an additional, selected, and preferably dry, ingredient which is added thereto at 60. In one example, a highly purified isoflavone may be added to bring the isoflavone produced by steps 20–48 to a desired specification. In another example, a number of lots of powder may be blended together in order to average out differences in several product runs.

The dry powder and added ingredient blended at 62 may also include food ingredients or the like. The food ingredient may be any in a group including sweetners, cocoa ingredients, starch, maltodextrin, animal protein, milk protein, soy flour, soy protein concentrate, plant and animal proteins, soy protein isolate, soy fiber, fluid lecithin, granular lecithin, polysaccharides, starches, fats and oils, phytosterols, phytosterol esters, phytostanols, phytostanol esters, mixed tocopherols, d,I-alpha tocopherol, sweetners and derivatives, lignans, catechins, carotenoids, d-alpha tocopherol, tocotrienols, and mixed thereof.

In fact, food products themselves may be added at 60 in order to incorporate the isoflavones produced by the invention into foods such as: cereals, yogurt, margarine, health bars, tea and other beverages, meal replacements, soup, pasta, ice cream, bakery products, dairy products, medical foods, nutritional supplements, and the like.

While the foregoing blending has been described in connection with the principal end product of the inventive process, it is also applicable to a blending with the separated impurities and solvents.

The advantages of the process of FIGS. 5 and 6 is that it permits storage, better blending, and closer control over the specifications of the final product so that quality control is easier. In addition, drying the product at 40 requires less equipment usage since it is no longer necessary to have large batches of product sitting in large tanks for long periods of time during which crystals are formed and separated from their mother liquid.

Since the product may be held in storage in a dry form, there is less time for contamination to occur.

The dry product better enables a final usage in many forms such as pills, liquids, ingredients for various foods, and the like.

EXAMPLES

1) Ultrafiltration of Soy Solubles

Using a stainless steel steam-heated immersion coil, soy solubles (15.26 kg) were heated to a constant temperature of about 80° C. The soy solubles were then passed through a model 92-HFK-131-UYU spiral wound, polysulfone, 10,000 nominal molecular weight cut-off ultrafiltration membrane (Koch Membrane Systems, Inc., St. Charles, Ill.) by using a peristaltic pump. Back pressure on the exit side of the membrane was adjusted by means of a hand-tightened clamp to provide a permeate flow of 70 ml/minute. Ultrafiltration was continued until 9.4 kg of permeate was collected leaving 4.8 kg of retentate. Isoflavone profiles of the various fractions were shown below:

| Sample | Weight (kg) | % Solids | Total Isoflavones (g) | Genistin (g) | daidzein (g) |
|---|---|---|---|---|---|
| Solubles | 15.26 | 8.65 | 11.45 | 4.01 | 4.30 |
| Retentate | 4.8 | 11.5 | 4.63 | 1.75 | 1.67 |
| Permeate | 9.4 | 7.7 | 6.6 | 2.29 | 2.68 |

2) Diafiltration of UF Retentate

Ultrafiltration retentate (80° C. initial temperature) was subjected to ultrafiltration as described in Example 1, except that 4.8 kg of tap water (25° C.) was fed into the retentate at a feed rate which is the same as the permeate rate or flux of the permeate that was being produced. The retentate was then further ultrafiltered to a final weight of 1.93 kg. Isoflavone profiles of the various fractions is shown below:

| Sample | Weight (kg) | % Solids (g) | Total Isoflavones (g) | Genistin (g) | daidzein (g) |
|---|---|---|---|---|---|
| Retentate Diafilt. | 4.8 | 11.5 | 4.63 | 1.75 | 1.67 |
| Permeate Diafilt. | 7.25 | 4.28 | 2.12 | 0.72 | 0.96 |
| Retentate | 1.93 | 12.26 | 2.14 | 0.91 | 0.58 |

3) Adsorption and Recovery of Isoflavones From a Resin

A glass liquid-chromatography column (2.54 cm i.d.) was slurry packed in 70% ethanol with Dow XUS 40323 divinylbenzene, ethylvinylbenzene copolymer resin. The resin was cleaned with an additional 500 mL of 70% wt ethanol followed by 0.1% wt NaOH (500 mL) and water (500 mL). The resin was then back-flushed with water until the resin bed volume had expanded by about one half of its originally packed volume in order to partition the resin by size. The final packed volume was 100 mL. Fresh UF permeate (2000 mL or 20 column volumes) at an initial temperature of 60° C. was fed through the resin bed at 6 column volumes/hour or 10 mL/minute. The resin bed was washed with 500 mL of water at 10 mL/minute to remove residual sugars and other impurities. Isoflavones were then eluted from the resin with a linear gradient of 20–95% ethanol (500 mL total) at 10 mL/minute. Next, the entire ethanolic isoflavone containing fraction was vacuum dried to obtain a product with the following profile:

| Sample | Weight (g) | Total Isoflavones (g) | Genistin (g) | daidzein (g) |
|---|---|---|---|---|
| Column Product | 6.56 | 2.2 | 0.92 | 0.83 |

4) Elimination of Undesirable Taste and Color

The process described in U.S. Pat. No. 5,679,806 results in a product which is enriched in isoflavone fractions at a concentration of 30–50% wt on a dry basis. This product has a reddish-brown color and has bitter flavor. Although its high isoflavone content makes it a desirable product for many applications, its color and flavor may preclude its use in certain types of products where sensory attributes are important, such as foods and beverages.

This example produces a product which is lighter in color and bland in flavor, with a higher isoflavone concentration which occurs upon removal of the color and flavor components. The new product produced by this example also has an increased utility because smaller quantities of the starting material are required to deliver approximately the same amount of isoflavones. Also, the improvement in flavor and color enables a use of the isoflavones in a wide variety of applications, such as foods, beverages, medical foods, and certain dietary supplement products.

Soy solubles ultrafiltered at 22 produce a permeate having approximately 1–20% solids. This leads to a drying end step that may be carried out by any suitable means, the preferred means being spray drying.

More particularly, at 28, this permeate was passed through a liquid chromatography column containing a polystyrene divinyl-benzene resin ("Amberlite-XAD-4") to adsorb isoflavones. Thereafter, at 30, the resin was washed with water. Then, the isoflavones were eluted from the resin 32 with aqueous ethanol (in the range of 20–100% volume of alcohol and preferably about 70% volume ethanol). Next, the ethanol was evaporated at stage 38 to about 1.098% wt solids in order to produce a feed to a dryer at 38. In this example, the evaporator was heated by direct steam injection. While any of many types of dryers may be used, preferably a spray dryer is used at 40.

However, with this example, instead of completion of spray drying after elution step 32, the product was treated in the following manner:

19.29 kg spray drier feed, containing a visible amount of precipitated material was evaporated under vacuum in order to remove water and increase solids content 200 g samples were taken both prior ("Spray Dryer Feed") and during ("Concentrate 1" and "Concentrate 2") evaporation in order to monitor the effect of solids content on the isoflavone recovery. These samples were allowed to cool to room temperature (about 20° C.) and subsequently centrifuged at 900×G for about 5 minutes in order to sediment the precipitate. The resulting supernatant was poured off of the sedimented precipitate and then the precipitate was dried at 140° F. (60° C.) for 16 hours. Next, all samples were analyzed for isoflavone content by HPLC, and were found to be a light cream color and to have a bland taste.

The recovery of isoflavones during the test carried out in this example are set forth in the following tables. Table 1 gives the isoflavone recovery during a processing of three samples designated A–C. The samples are designated A were taken from a spray-dryer feed, samples B (Concentrate I) were taken from the evaporator at step 38 during an early stage of the evaporation, and samples C (Concentrate II) were taken from the evaporator during a later stage of the evaporation. For each of the samples, the tests were run, respectively, on a complete dryer feedstream (A), upon a supernatant which was poured off after decanting (B), and upon the precipitate (C).

The solids prior to centrifugation and the amounts of isoflavones that were recovered are set forth in Table 2. The breakdown of the isoflavones that were recovered are set forth in Table 3. The conclusion is that each of the tests shows results that are attractive for certain uses. Therefore, the practitioner will select the particular process which best reflects the results that he seeks.

TABLE 1

| | Sample | % Solids (Soy Whey) | Isoflavones ppm | Weight (g) | Total Isoflavones |
|---|---|---|---|---|---|
| A | Spray Dryer Feed | 1.098 | 5583.4 | 200.04 | 1.117 |
| A | Spray Dryer Feed Supertant | 0.848 | 2937.6 | 192.04 | 0.564 |
| A | Dried Spray Dryer Feed Precipitate | 100.00 | 849624.8 | 0.56 | 0.477 |
| B | Concentrate I | 1.814 | 9313.5 | 200.01 | 1.863 |
| B | Concentrate I Supertant | 1.308 | 3980.8 | 185.35 | 0.738 |
| B | Dried Concentrate I Precipitate | 100.0 | 891696.8 | 1.21 | 1.077 |
| C | Concentrate II | 4.633 | 23404.6 | 200.00 | 4.681 |
| C | Concentrate II Supernatant | 3.173 | 8712.9 | 170.72 | 1.487 |
| C | Dried Concentrate II Precipitate | 100.0 | 838399.3 | 3.65 | 3.057 |

TABLE 2

| % Solids Prior to Centrifugation | % Recovery of Isoflavones in Centrifuged Precipitate |
|---|---|
| 1.098 (A) | 49.49 |
| 1.814 (B) | 60.39 |
| 4.633 (C) | 68.22 |

TABLE 3

| Isoflavone | Dried Spray Dryer Feed Precipitate (ppm) A | Dried Concentrate I Precipitate (ppm) B | Dried Concentrate II Precipitate (ppm) C |
| --- | --- | --- | --- |
| daidzein | 347109.3187 | 422936.0742 | 412219.9703 |
| Glycitin | 37066.4070 | 43523.2763 | 44077.5906 |
| Genistin | 408166.8156 | 357561.8669 | 305240.8582 |
| Malonyl-daidzein | 4195.0096 | 6128.8092 | 7556.7644 |
| Malonyl-Glycitin | 67.4223 | 96.0281 | 157.1695 |
| Acetyl-daidzein | 26792.2537 | 32540.1269 | 35771.3900 |
| Acetyl-Glycitin | 389.8314 | 794.5519 | 1522.1046 |
| Malonyl-Genistin | 1755.5026 | 2469.0077 | 3581.2460 |
| Daidzein | 2952.0643 | 3814.0725 | 3615.3280 |
| Acetyl-Genistin | 18471.3792 | 19019.5539 | 21794.8883 |
| Glycitein | 1031.0817 | 1039.2615 | 1154.3133 |
| Genistein | 1627.7324 | 1774.1731 | 1707.7167 |
| Total ppm (%) | 849624.8 (85.0%) | 891696.8 (89.2%) | 838399.3 (83.8%) |

5) Soy Whey Starting Material

The staring material for these examples is soy whey. Soy whey is defined as a liquid from the isoelectric or the divalent precipitation of the solubilized fraction from the processing of soybeans into soyfoods.

EXAMPLE A

Process Outline:

SOY WHEY (FIG. 3 at 20)→ULTRAFILTRATION (100,000 Mol. Wt. cut-off) (FIG. 3 at 22)→PERMEATE (FIG. 3 at 26)→REVERSE OSMOSIS (concentration) (FIG. 4 at 27)→ADSORPTIVE RESIN (FIG. 3 at 28)→WATER WASH RESIN (FIG. 3 at 30)→ELUTE PRODUCT WITH AQUEOUS AlCOHOL (FIG. 3 at 32).

Adsorption and Recovery of Isoflavones From a Resin Utilizing Soy Whey As a Starting Material, Raw Material and End Product Description:

| Sample | Total Wt. (kg) | Total Isoflavones (g) | Isoflavone Conc. (%) |
| --- | --- | --- | --- |
| Reverse Osmosis Concentrate (ROC) | 882.49 | 219.74 | 0.0249 |
| Isoflavone Concentrate Product | 0.4223 | 155.17 | 36.744 |

A plurality of 1800 ml stainless steel liquid chromatography columns were slurry packed with "Amberlite" XAD-4 divinyl-benzene copolymeric polymeric absorbent resin. The resin was cleaned repeatedly with 80% wt. ethanol, water and 0.1–0.3% wt. NaOH solution. The final bed volume (BV) of resin in each column was 1500 ml.

The reverse osmosis concentrate (ROC) was heated to a temperature of 80° C. Two columns (2×BV=BV2) were fed in series of 600 ml/min. and received a total of 36 liters (12 BV2) of ROC. Individual columns than received a 60° C. water wash at 100 ml/min. (3000 ml. or 2 BV) to remove residual sugars and other impurities. Isoflavones were then eluted from the washed columns with 60° C., 80% wt. ethanol at 90 ml/min. (5400 ml or 3.6 BV) producing an ethanolic isoflavone fraction. The ethanol was evaporated and removed from the isoflavone fraction. The isoflavone fraction was then spray dried, resulting in a total of 422.3 g of a 36.745% isoflavone powder.

EXAMPLE B

Process Outline

SOY WHEY (FIG. 3 at 20)→ULTRAFILTRATION (100,000 Mol. Wt. cut-off) (FIG. 3 at 22)→PERMEATE (FIG. 3 at 26)→REVERSE OSMOSIS (concentration) (FIG. 4 at 27)→ADSORPTIVE RESIN (FIG. 3 at 28)→WATER WASH RESIN (FIG. 3 at 30)→ELUTE PRODUCT WITH AQUEOUS ALCOHOL (FIG. 3 at 32)→EVAPORATE AQUEOUS ETHANOL (produce aqueous isoflavone solution) (FIG. 3 at 38)→AQUEOUS ISOFLAVONE SOLUTION UTILIZATION→

1) DRY AQUEOUS ISOFLAVONE SOLUTION (FIG. 3 at 40)→PRODUCT #1, or

2) COOL AQUEOUS ISOFLAVONE SOLUTION→CENTRIFUGE AQUEOUS ISOFLAVONE SOLUTION (isolate crystals) (FIG. 3 at 42)→DRY CRYSTALS (FIG. 3 at 40)→PRODUCT #2.

Absorption and Recovery of Isoflavones from a Resin Utilizing Soy Whey as a Starting Material Raw Material and End Product Descriptions

| Sample | Total Wt. (kg) | Total Solids (%) | Total Isoflavones (g) | Isoflavone Conc. (%) |
| --- | --- | --- | --- | --- |
| Reverse Osmosis Concentrate (ROC) from soy whey | 646.65 | 3.24 | 221.80 | 0.0343 |
| Isoflavone Fraction #1 | 7.73 | 4.62 | 72.03 | 0.9318 |

A plurality of 1800 ml stainless steel liquid chromatography columns were slurry with "Amberlite" XAD-4 divinyl-benzene copolymer absorbent resin. The resin was cleaned repeatedly with 80% wt. ethanol, water and 0.1–0.3% wt. NaOH solution. The final bed volume (BV) of resin in each column was 1500 ml.

The reverse osmosis concentrate (ROC) was heated to a temperature of 80° C. Each column received 36 L (24 BV) of ROC at 225 ml/min. Individual columns then received a 60° C. water wash at 100 ml/min. (4000 ml. or 2.7 BV) to remove residual sugars and other impurities. Isoflavones were then eluted from the washed columns with 60° C., 60% wt. ethanol at 90 ml/min. (7200 ml or 4.8 BV) producing an ethanolic isoflavone fraction. This sequence was repeated until a total of 654 L of ROC had been fed through the columns with the absorbed isoflavones then recovered in the ethanolic fraction. The ethanol was evaporated and removed, producing isoflavone fraction #1. Fraction #1 had two possibilities for utilization: 1) drying fraction #1 to produce Product #1, or 2) to be used as a raw material to recover isoflavone crystals to produce a higher % wt. isoflavone, Product #2.

Recovery of Isoflavones from the Concentrated Column Effluent (Fraction #1)

The isoflavone fraction #1 was cooled over a 2 hour period to a temperature of 25° C. resulting in isoflavone crystal formation. A sample of the cooled isoflavone fraction #1 was then centrifuged at 900×G for 10 min. to pellet the isoflavone crystals. Next, the supernatant was poured off. The remaining pellets were vacuum dried (140° F., 16 hours)

and analyzed for isoflavone content. Further purification of the pellets can be obtained by water washing and repeated centrifugation.

| Sample | Weight (g) | Total Isoflavones (g) | Isoflavones (%) |
|---|---|---|---|
| Isoflavone Product #1 (Isoflavone fraction #1 on a dry weight basis) | 357.13 | 72.03 | 20.2 |
| Isoflavone Product #2 | 3.02 | 2.05 | 67.9 |

The process that is described herein has the advantage of utilizing another common soy processing by-product, soy whey, as a starting material for the manufacture of isoflavone concentrates. When soy whey is used as the starting material, products produced from drying the concentrate column effluent can be approximately 20–40% wt., and preferably in the upper part of the range or 35–40% wt. isoflavone fractions. These products are reddish-brown in color and bitter in flavor. The high isoflavone content makes it useful for applications such as tableting and inclusion into some foods. However, where sensory attributes are important, further processing of the concentrated column effluent material can be done to produce isoflavone concentrate more suited to food and beverage additions.

Concentrated column effluents from the processing of soy whey and soy molasses can be centrifuged or filtered and then dried to produce a new isoflavone concentrate product. The new product is lighter in color, has a less bitter taste and is higher in isoflavone concentration. These improvements allow for a wider range of uses of soy whey and molasses in foods, beverages, medical foods and dietary supplements where sensory attributes are more of a concern.

6) Improved Recovery of Isoflavones from a Dried Impure Product

This example produces a solid product that is lighter in color and bland in flavor with a higher isoflavone concentration that occurs upon removal of the color and flavor components than that produced by the process described in U.S. Pat. No. 5,679,806. The new product produced by this example also has an increased utility because smaller quantities are required to deliver approximately the same amount of isoflavones. Also, the improvement in flavor and color enables a use of the isoflavones in a wide variety of applications, such as foods, food ingredients, beverages, medical foods, and certain dietary supplement products.

Another advantage of this process comes from the production of a readily water-soluble supernatant or filtrate fraction, which is different in isoflavone profile from the solid product. This product has an isoflavone ratio with proportionally higher levels of daidzein than the solid product, which solid product has a ratio that favors genistin. This water-soluble fraction is also expected to contain saponins. This water-soluble fraction can be further treated or used in applications where a higher level of water-solubility and/or daidzein or saponins may be desired.

The 30–50% by weight isoflavone spray dried product produced as described in U.S. Pat. No. 5,679,806 is the starting material for this process. Different lots of commercially produced spray-dried product were slurried with water. Slurried solutions were then filtered or centrifuged with or without adjusting the pH in the solutions so as to result in a solid product and the filtrate or supernatant. The separated fractions (the solid product and the filtrate or supernatant) were then dried and evaluated for isoflavone concentration. Laboratory parameters were also applied on a pilot-scale to test commercial feasibility of the process in producing the two fractions.

EXAMPLE A

Three samples were prepared from Lot A (Feed is Spray Dried Product), as seen in Table 4 and as follows:

Three 10 g samples of Feed were weighed, then diluted with deionized water (70° C.) at the following three ratios (weight of Feed:weight of water): 1:2 (20 g), 1:4 (40 g) and 1:6 (60 g).

Samples were mixed to dispersion and immediately filtered through an 11 micron, 6% open area filter cloth on a buchner funnel, into flask, under vacuum (20"Hg).

Filter cakes and filtrates were recovered, weighed and vacuum dried (24"Hg) at 70° C. for 16 hrs.

Dried samples were weighed, ground and then analyzed for isoflavone content.

The procedure was repeated utilizing a 5 micron, 2% open area filter cloth.

The results are reported in Table 4, and show that the cake is much enriched for isoflavones. The greatest degree of enrichment is seen at the higher dilutions, regardless of the size of the filter.

EXAMPLE B

Two samples were prepared from Lot B (Feed is Spray Dried Product, Table 4) as follows:

100 g Feed weighed into 200 g of deionized water (20° C.) at a ratio of 1:2 and mixed to dispersion (approximately 30 min.).

Another sample was prepared by weighing 50 g Feed into 500 g of deionized water (20° C.) at a ratio 1:10 and mixed to dispersion (approximately 30 min.).

The pH of each sample was found to be about 4.0 and then a weighed aliquot of each dispersion sample was centrifuged at 2000 rpm for 5 min.

Each centrifuged sample was then split into two weighed portions of supernatant and pellet.

After dispensing the first aliquot, the 1:2 and 1:10 dispersions were both adjusted to a pH of approximately 9.0 with 50% Sodium Hydroxide.

Weighed aliquots were centrifuged at 2000 rpm for 5 min.

Each centrifuged sample was then split into two weighed portions of supernatant and pellet.

Samples were then dried under vacuum (24"Hg) at 70° C. for at least 16 hrs.

This procedure was repeated for both dilutions (ratio 1:2 and 1:10) with a water temperature of 70° C., and all else held constant.

The results are reported in Table 4, and show that the cake is much enriched for isoflavones. As with Example A, a greater enrichment is generally seen at the higher dilutions—especially at the higher pH. Increased temperature moderately increases isoflavone enrichment.

EXAMPLE C

Large scale testing of the filtration procedure was done utilizing a pilot-scale rotary vacuum filter (RVF).

Rotary vacuum drum was fitted with an 11 micron, 6% open area filter cloth.

2.0 kg of Lot C (Feed is Spray Dried Product, Table 4) was dispersed into a total of 10 kg, 20° C. tap water (ratio 1:5) with a total mix time of 60 min.

The mixed sample was fed to the trough below the rotary vacuum drum to a steady level which maintained surface contact with the bottom of the drum.

The vacuum pulled sample onto the moving drum with the filter cloth, building up a layer of isoflavones.

A portion of the isoflavone layer was then cut off as the barrel rotated around at a rate of 0.8–1.0 rpm.

Vacuum to barrel at start of test was 6"Hg and steadied to 16"Hg for duration of filtration test.

Process produced two distinct products: cake and filtrate.

Samples were freeze dried prior to isoflavone analysis.

As seen in Example C of Table 4, the cake is much enriched for isoflavones at the pilot-scale level of treatment.

TABLE 4

Isoflavone Concentrate From Reconsituted Spray Dried Product

| Ex. | Dilution feed: water | % T.S. | Test Filter or Centrifuge | Condition water temp. | pH | Feed % isoflavone | Cake/ Pellet % isoflavone | Super/ Filtrate % isoflavone |
|---|---|---|---|---|---|---|---|---|
| A | 1:2 | 33.33 | 11 micron 6% open area | 70° C. | not adjusted | 47.66 Lot A | 75.06 | 31.35 |
|   | 1:4 | 20 |   |   |   |   | 81.58 | 31.84 |
|   | 1:6 | 14.3 |   |   |   |   | 85.3 | 31.8 |
|   | 1:2 | 33.33 | 5 micron 2% open area |   |   |   | 79.3 | 30.24 |
|   | 1:4 | 20 |   |   |   |   | 82.51 | 27.58 |
|   | 1:6 | 14.3 |   |   |   |   | 83.92 | 31.63 |
| B | 1:2 | 33.33 | 5 min. at 2000 rpm | 20° C. | 4.56 9 4.16 8.92 | 38.71 Lot B | 62.18 64.99 | 29.45 28.72 |
|   |   |   |   | 70° C. | 4.35 8.99 |   | 69.87 65.22 | 26.66 25.77 |
|   | 1:10 | 9.09 |   | 20° C. | 4.15 8.97 |   | 60.43 83.92 | 26.06 25.95 |
|   |   |   |   | 70° C. |   |   | 68.06 83.78 | 27.29 25.8 |
| C | 1:5 | 16.7 | RVF 11 micron 6% open area | 20° C. tap water | not adjusted | 50.14 Lot C | 82.8 | 26.7 |

Those who are skilled in the art will readily perceive how to modify the invention. Therefore, the appended claims are to be construed to cover all equivalent structures which fall within the true scope and spirit of the invention.

The claimed invention is:

1. A process for separating a plurality of forms of isoflavone fractions consisting of one or more forms of isoflavones in an aqueous plant starting material, said process comprising the steps of:
   (a) heating an aqueous plant starting material to a constant temperature selected on a basis of an aqueous solubility for a desired isoflavone fraction containing at least one isoflavone that is to be recovered;
   (b) passing the heated starting material of step (a) through an ultrafiltration membrane to obtain a permeate, the membrane having a cut-off which passes said at least one isoflavone fraction;
   (c) treating the permeate with an adsorptive material;
   (d) washing the material of step (c) in water;
   (e) eluting said at least one isoflavone fraction from the water-washed adsorptive material of step (d) with an aqueous alcohol solvent to form a stream;
   (f) removing the aqueous alcohol from the stream formed during the elution of step (e) so as to promote crystallization of said at least one isoflavone fraction;
   (g) drying the product of step (f) to form dry particles;
   (h) adding a solvent to the dried product of step (g) to form a mixture; and
   (i) separating the crystallized isoflavone fraction containing said at least one isoflavone from the mixture of step (h) to provide a product in a dry or liquid form.

2. The process of claim 1, wherein the dried product of step (g) is stored before step (h).

3. The process of claim 1, wherein the solvent of step (h) is selected from the group consisting of tap water, deionized water, and distilled water, ethanol, isopropanol, methanol, and combinations of these solvents.

4. The process of claim 3, wherein the solvent is tap water.

5. The process of claim 1, wherein step (i) is followed by a process wherein the product of step (i) is blended with a product selected from a group consisting of a food product, a food ingredient, a medical food, or a dietary supplement.

6. The process of claim 5, wherein the food ingredient is selected from the group consisting of sweetners, starch, maltodextrin, milk proteins, animal protein, soy flour, soy protein concentrate, soy protein isolate, and other edible proteins, soy fiber, fluid lecithin, granular lecithin, fats and oils, phytosterols, phytosterol esters, phytostanols, phytostanol esters, tocopherols, d,I-alpha tocopherol, d-alpha tocopherol, tocotrienols, lignans, catechins, carotenoids, and mixtures thereof.

7. The process of either one of claim 1 or 5 wherein the product of step (i) is mixed with a food selected from a group consisting of cereal, yogurt, margarine, health bars, tea, meal replacements, soups, pasta, frozen desserts, dairy products, bakery products, and medical foods.

8. The process of claim 1, wherein a step of blending in at least one ingredient is incorporated in a step selected from a group consisting of steps (g), (h), and (i).

9. The process of claim 8, wherein the at least one ingredient is selected from the group consisting of sweetners, starch, maltodextrin, milk protein, animal protein, soy flour, soy protein concentrate, soy protein isolate, and other edible proteins, soy fiber, fluid lecithin, granular lecithin, fats and oils, phytosterols, phytosterol esters, phytostanols, phytostanol esters, mixed tocopherols, d,I-alpha tocopherol, d-alpha tocopherol, lignans, catechins, carotenoids, tocotrienols and mixtures thereof.

10. The process of claim 8 wherein said at least one ingredient is selected from a group consisting of cereal, yogurt, margarine, health bars, tea, meal replacements, soup, pasta, frozen desserts, dairy products, bakery products, and medical foods.

11. The process of claim 1 and the added step of incorporating a product from at least one of the steps (g), (h), or (i) into a product selected from a group consisting of a dietary supplement or a dietary supplement ingredient or a medical food ingredient.

12. The process of claim 1, wherein the solvent is at a temperature between about 4° C. and 95° C.

13. The process of claim 12, wherein the solvent is at a temperature between about 20° C. and 40° C.

14. The process of claim 1, wherein the solvent is at a pH between about 2 and 10.

15. The process of claim 14, wherein the solvent is at a pH between about 6 and 8.

16. The process of claim 1 wherein step (i) includes a process selected from a group consisting of decanting, hydrocloning, centrifuging and filtering.

17. The process of claim 1 wherein said separation of step (i) comprises the step of centrifuging the mixture of step (h).

18. The process of claim 1 wherein said separation of step (i) comprises the step of filtering crystals from the mixture of step (h).

19. The process of claim 1 wherein the at least one isoflavone fraction separated in step (i) is a light tan color.

20. The process of claim 1 wherein the isoflavone fraction separated in step (i) has a bland taste.

21. The process of claim 1 wherein the end product of said process has an isoflavone fraction concentration of at least 50% preferred weight on a dry weight basis.

22. The process of claim 1 wherein the starting material is soy molasses and the end product of step (i) of said process has an isoflavone fraction concentration in a range of about 70–90% weight on a dry weight basis.

23. The process of claim 1 wherein the starting material is soy whey and the end product of step (i) of said process has an isoflavone fraction concentration in a range of about 50–80% weight on a dry weight basis.

24. A process for separating isoflavone fractions in an aqueous plant starting material, said process comprising the steps of:
  (a) heating an aqueous plant starting material at a constant temperature selected on a basis of an aqueous solubility for at least one desired isoflavone fraction that is to be recovered;
  (b) passing the starting material of step (a) through an ultrafiltration membrane to obtain a permeate, the membrane having a cut-off which passes said at least one isoflavone fraction;
  (c) treating the permeate with an adsorptive material;
  (d) eluting said at least one adsorbed isoflavone fraction from the treated material of step (c) with aqueous alcohol;
  (e) removing the aqueous alcohol from the treated material used during step (d) in order to increase the solid basis of said at least one isoflavone fraction; and
  (f) drying the at least one isoflavone fraction in step (e);
  (g) adding a solvent to rehydrate the dried product of step (f) to form a second mixture; and
  (h) separating the solid basis of said at least one isoflavone fraction from the second mixture to provide an output product.

25. The process of claim 24 and the further comprising the step of adding and blending a selected amount said isoflavone fraction of step (f) in order to bring said isoflavone fraction to a predetermined specification.

26. The process of claim 18, wherein the product of step (i) is dried by spray drying.

27. The process of either claim 1 or 24 wherein there are a plurality of isoflavone fractions recovered in both step (a) and after said separation of said isoflavone fraction after the last step in said process.

28. The process of either claim 1 or 24 wherein the process is a continuous process further comprising the sub-steps of:
  providing a plurality of liquid chromatography columns in step c, each of which is filled with an adsorptive resin; and
  switching the permeate of step (b) and washing the adsorptive resin of step (c) so that at least one of said plurality of columns is loading while at least one other of said plurality of columns is washing; and
  switching the wash so that at least one of said plurality of columns is washing while at least one other of said plurality of columns is eluting.

29. The process of either claim 1 or 24 wherein said adsorptive material of step (c) is a styrene divinyl-benzene copolymer.

30. The process of either claim 1 or 24 wherein said adsorptive material of step (c) is a resin selected from a group consisting of ionic or non-ionic resin.

31. The process of either claim 1 or 24 wherein said adsorptive material of step (c) is selected from a group consisting of ethylvinylbenzene-divinyl-benzene, styrene-divinyl-benzene copolymers and polystyrene polymers.

32. The process of claim 1 wherein said step (i) is carried out by sedimenting a liquid obtained from step (h), decanting off a resulting supernatant, and processing the sedimented precipitate.

33. The process of claim 24 wherein the second mixture contains a visible amount of precipitated material.

34. A process for the production of a selected group of isoflavone fractions from plant matter, said process comprising the steps of:
  (a) obtaining a starting material by heating an aqueous stream including water soluble plant material to produce a stream selected from a group consisting of soy molasses and soy whey, said heat being a temperature selected to solubilize a plurality of isoflavone fractions in said stream;
  (b) ultrafiltering the stream resulting from step (a), said filtration being carried out by a membrane having a cut-off which produces a permeate stream containing said plurality of isoflavone fractions solubilized in step (a);
  (c) processing said permeate stream from step (b) by first adsorbing with an adsorbing resin at least some of said solubilized isoflavone fractions and then washing said adsorbing resin to remove residual sugars and other water-soluble impurities;
  (d) eluting said washed adsorbing resin resulting from step (c) with an aqueous alcohol; and
  (e) removing said aqueous alcohol from an eluted stream of step (d) in order to produce a stream which is approximately 1–20% solids by weight;
  (f) drying the stream of step (e) to a powder state;

(g) adding a solvent to the dried powder of step (f) to dissolve impurities; and (h) separating the impurities and solvent from the plurality of isoflavone fractions to provide a product.

35. The process of claim 34 further comprising the steps of selecting an amount of an isoflavone to bring said powder of step (f) to a predetermined characteristic specification; and blending said powder of step (f) with said selected amount of isoflavones prior to said step (g).

36. The process of claim 34 wherein said adsorbing of step (c) is carried out in a plurality of liquid chromatography columns packed with a resin selected from a group consisting of ionic ethylvinylbenzene-divinyl-benzene copolymer, non-ionic ethylvinylbenzene-divinyl-benzene copolymer, ionic styrene-divinyl-benzene copolymer, non-ionic styrene-divinyl-benzene copolymer, ionic polystyrene, and non-ionic polystyrene.

37. The process of claim 36 wherein said selected resin is a polystyrene-divinyl-benzene copolymer.

38. The process of claim 34 wherein the temperature of the heat in step (a) is in the order of about 65°–95° C.

39. The process of claim 34 wherein said membrane used in said ultrafiltration of step (b) has a nominal molecular weight cut-off range of about 600–1,000,000.

40. The process of claim 38 wherein said membrane used in said ultrafiltration of step (b) has a nominal molecular weight cut-off range of 100,000 nominal molecular weight.

41. The process of claim 36 wherein said adsorbing process of step (c) is a continuous process using said plurality of liquid chromatography columns wherein at least one of said plurality of liquid chromatography columns is loading while another of said at least one of said columns is washing and while still another of said at least one of said columns is eluting in step (d).

42. The process of claim 34 wherein said stream of step (e) is cooled by evaporation to approximately 4 to 45° C. and is subjected centrifugation at about 900×g.

43. A process for extracting isoflavone enriched fractions from soy, comprising the steps of:

(a) obtaining and heating an isoflavone-containing starting material of soy to a temperature which solubilizes at least one isoflavone fraction;

(b) ultrafiltering said heated starting material to produce a permeate;

(c) subjecting said permeate of step (b) to reverse osmosis in order to concentrate said at least one isoflavone fraction;

(d) adsorbing said concentrate of step (c) in at least one liquid chromatography column containing an adsorptive resin;

(e) washing said at least one chromatography column with water; and (f) eluting the water-washed resin of step (e) with aqueous alcohol to form a stream;

(g) evaporating the aqueous alcohol from the stream;

(h) drying the evaporated stream of step (g) to provide at least one dry isoflavone fraction;

(i) adding a solvent to the dried stream of step (h) to dissolve impurities; and (j) separating the impurities and solvent from the isoflavone-enriched fraction to provide a product.

44. The process of claim 43 and the added step of blending a selected amount of an isoflavone fraction with said fraction dried in step (h).

45. The process of claim 43 wherein the ultrafiltering of step (b) is carried out by a membrane having 100,000 molecular weight cut-off.

46. The process of claim 43 wherein said at least one liquid chromatography column of step (d) is packed with divinyl-benzene copolymer adsorbent resin.

47. The process of claim 43 wherein the adsorbing of the reverse osmosis concentrate of step (c) is carried out at approximately 65–95° C.

48. The process of claim 43 wherein the elution of step (f) is carried out at approximately 40–70° C. with aqueous ethanol.

49. The process of claim 43 wherein said reverse osmosis concentrate of step (c) has an isoflavone concentration in a range of about 0.01–0.1% wt.

50. The process of claim 43 wherein the starting material is soy whey and the product of step (h) of said process has an isoflavone fraction concentration of approximately 20–40% weight on a dry weight basis.

51. The process of claim 43 wherein the starting material is soy whey and the product of said process of step (h) has an isoflavone fraction concentration of approximately 35–40% weight on a dry weight basis.

52. The process of claim 43 wherein the starting material is soy whey and the product of step (j) has an isoflavone fraction concentration in an approximate range of 50–80% weight on a dry weight basis.

53. The process of one of the claims 1, 24, 34, and 43 wherein the last separating step is followed by another step of drying said product.

54. The process of claim 34 wherein impurities and solvents separated from said product of step (h) is enriched in saponins and forms of daidzein.

55. The process of claim 43 wherein impurities and solvents separated from said product of step (j) is enriched in saponins and forms of daidzein.

56. A product made by the process of any one of the claims 1, 24, 34, and 43.

57. The process of either claim 34 or 43 wherein the said product is enriched in forms of genistein.

58. The process of either claims 54 or 55 and the further step of drying the separated impurities and solvents.

59. The product made by the process of claim 58.

60. The process of blending the product of claim 59 with a product selected from a group consisting of a food product, a food ingredient, a medical food, or a dietary supplement.

61. The process of blending the product of claim 59 with a food ingredient selected from the group consisting of sweetners, starch, maltodextrin, milk proteins, animal protein, soy flour, soy protein concentrate, soy protein isolate, and other edible proteins, soy fiber, fluid lecithin, granular lecithin, fats and oil, phytosterols, phytosterol esters, phytostanols, phytostanol esters, tocopherals, d,l-alpha tocopherol, d-alpha tocopheral, tocotrienols, lignans, catechins, carotenoids, and mixtures thereof.

62. The process of blending the product of claim 59 with a food selected from a group consisting of yogurt, margarine, health bars, tea, meal replacements, soups, pasta, frozen desserts, dairy products, bakery products, and medical foods.

* * * * *